United States Patent
Ishida et al.

(10) Patent No.: US 8,309,752 B2
(45) Date of Patent: Nov. 13, 2012

(54) PROCESS FOR PRODUCTION OF MANDELONITRILE COMPOUND

(75) Inventors: Hajime Ishida, Saijo (JP); Masaji Hirota, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 84 days.

(21) Appl. No.: 13/001,075

(22) PCT Filed: Jun. 24, 2009

(86) PCT No.: PCT/JP2009/062025
§ 371 (c)(1),
(2), (4) Date: Dec. 23, 2010

(87) PCT Pub. No.: WO2009/157589
PCT Pub. Date: Dec. 30, 2009

(65) Prior Publication Data
US 2011/0118498 A1  May 19, 2011

(30) Foreign Application Priority Data

Jun. 26, 2008 (JP) ................................. 2008-167083
Jan. 23, 2009 (JP) ................................. 2009-012862

(51) Int. Cl.
*C07C 253/10* (2006.01)
(52) U.S. Cl. ...................................................... 558/315
(58) Field of Classification Search ............... 558/315
See application file for complete search history.

(56) References Cited

U.S. PATENT DOCUMENTS

2008/0214861 A1   9/2008   Kozono et al.

FOREIGN PATENT DOCUMENTS

| JP | 2-17164 A | 1/1990 |
| JP | 07-033727 A | 2/1995 |
| JP | 2005-232105 A | 9/2005 |

OTHER PUBLICATIONS

English Translation of the Written Opinion of the International Searching Authority for PCT/JP2009/062025, dated Sep. 1, 2009.
Tanaka et al., "The Cyclic Dipeptide cyclo [(S)-Phenylalanyl-(S)-histidyl] as a Catalyst for Asymmetric Addition of Hydrogen Cyanide to Aldehydes", Journal of Organic Chemistry, vol. 55, No. 1, pp. 181-185, 1990.
Peng et al., "Cyanohydrintion Catalyzed by Chiral Cyclodipeptide Cyclo (L-Leu-L-His)", Jiangsu Chemical Industry vol. 33, No. 3, pp. 40-41 and 45, 2005.

*Primary Examiner* — Kristin Bianchi
(74) *Attorney, Agent, or Firm* — Birch, Stewart, Kolasch & Birch, LLP

(57) ABSTRACT

A method for producing a compound represented by the following formula (2)

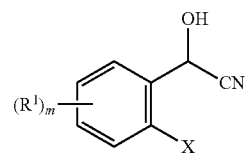

(2)

(wherein, X, $R^1$ and m represent respectively the same meaning as described below)
which comprises reacting a compound represented by the following formula (1)

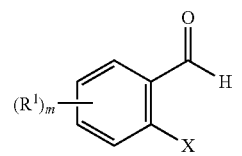

(1)

(wherein, X represents an optionally substituted alkyl group or the like. $R^1$ represents an optionally substituted alkyl group or the like. m represents an integer of 0 to 4. When m represents an integer of 2 to 4, $R^1$s may be the same or different from each other)
with hydrogen cyanide in an amount of 1.2 to 5 mol with respect to 1 mol of the compound, in the presence of an organic base, in an organic solvent.

5 Claims, No Drawings

PROCESS FOR PRODUCTION OF MANDELONITRILE COMPOUND

TECHNICAL FIELD

The present invention relates to a method for producing a mandelonitrile compound.

BACKGROUND ART

As the method of producing a mandelonitrile compound, for example, JP-A No. 7-33727 describes a method which comprises reacting a benzaldehyde compound and hydrogen cyanide in the presence of an alkali metal salt in a water solvent. Further, JP-A No. 2005-232105 discloses a method which comprises reacting a benzaldehyde compound and hydrogen cyanide in the presence of sodium carbonate or sodium acetate in a water solvent.

DISCLOSURE OF THE INVENTION

In the above-described conventional methods, however, when the benzaldehyde compound has a substituent at an ortho position, the substituent hinders the reaction, and the yield of a mandelonitrile compound is not satisfactory in some cases.

The present invention has an object of providing a method for producing a mandelonitrile compound in good yield from a benzaldehyde compound having a prescribed substituent at an ortho position.

The present inventors have intensively studied and resultantly found that the above-described object can be attained by reacting a benzaldehyde compound having a prescribed substituent at an ortho position with hydrogen cyanide in an amount of 1.2 to 5 mol with respect to 1 mol of the benzaldehyde compound, in the presence of an organic base in an organic solvent, leading to completion of the present invention.

Thus, the present invention is related to a method for producing a compound represented by the following formula (2)

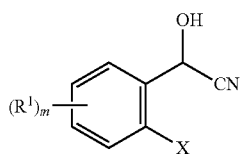

(2)

(wherein, X, $R^1$ and m represent respectively the same meaning as described below)
which comprises reacting a compound represented by the following formula (1)

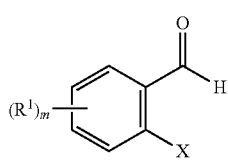

(1)

(wherein, X represents an optionally substituted alkyl group, optionally substituted alkenyl group, optionally substituted alkynyl group, optionally substituted phenyl group, optionally substituted phenoxy group or optionally substituted amino group. $R^1$ represents an optionally substituted alkyl group, optionally substituted alkenyl group, optionally substituted alkynyl group, optionally substituted alkoxy group, optionally substituted phenyl group, optionally substituted phenoxy group, optionally substituted amino group, hydroxy group, nitro group or halogen atom. m represents an integer of 0 to 4. When m represents an integer of 2 to 4, $R^1$s may be the same or different from each other).
with hydrogen cyanide in an amount of 1.2 to 5 mol with respect to 1 mol of the compound, in the presence of an organic base, in an organic solvent.

Effect of the Invention

According to the present invention, benzaldehyde compound (1) can be reacted with good conversion to produce mandelonitrile compound (2) in good yield.

BEST MODES FOR CARRYING OUT THE INVENTION

The present invention will be illustrated in detail below. The present invention is a method of producing mandelonitrile compound (2) which comprises reacting benzaldehyde compound (1) having a prescribed substituent at an ortho position with hydrogen cyanide in an amount of 1.2 to 5 mol with respect to the benzaldehyde compound (1), in the presence of an organic base in an organic solvent.

The benzaldehyde compound (1) has low reactivity because of a prescribed substituent at an ortho position, and sufficient conversion is not obtained with this compound in conventional methods. In the present invention, such benzaldehyde compound (1) having low reactivity and hydrogen cyanide are reacted at a ratio within the above-described range, in the presence of an organic base in an organic solvent, thereby improving the conversion of the benzaldehyde compound (1) and producing mandelonitrile compound (2) in good yield.

The optionally substituted alkyl group represented by X in the benzaldehyde compound (1) may be an unsubstituted alkyl group, or an alkyl group substituted with a halogen atom, hydroxy group, nitro group, amino group, alkoxy group, optionally substituted phenoxy group or the like. The unsubstituted alkyl group usually has about 1 to 12 carbon atoms. The substituted alkyl group has a substituent carried on an alkyl group usually having about 1 to 12 carbon atoms.

Examples of the optionally substituted alkyl group include unsubstituted alkyl groups such as a methyl group, ethyl group, n-propyl group, isopropyl group, n-butyl group, isobutyl group, s-butyl group, t-butyl group, n-pentyl group, n-hexyl group, n-octyl group, n-decyl group; haloalkyl groups such as a monofluoromethyl group, difluoromethyl group and trifluoromethyl group; hydroxyalkyl groups such as a hydroxymethyl group; nitroalkyl groups such as a nitromethyl group; aminoalkyl groups such as an aminomethyl group; alkoxyalkyl groups; and phenoxyalkyl groups.

Specific examples of the above-described alkoxyalkyl group include a methoxymethyl group, ethoxymethyl group, n-propoxymethyl group, isopropoxymethyl group, n-butoxymethyl group, isobutoxymethyl group, s-butoxymethyl group, and t-butoxymethyl group.

The alkyl group in the above-described phenoxyalkyl group has preferably 1 to 3 carbon atoms, more preferably 1 carbon atom. The phenoxy group in the above-described phenoxyalkyl group may be substituted. Examples of the above-described phenoxyalkyl group include groups represented by the following formula (3)

(wherein, $R^2$ represents an optionally substituted phenyl group).

The optionally substituted phenyl group represented by $R^2$ may be an unsubstituted phenyl group, or may be substituted with a substituent such as an alkyl group having 1 to 4 carbon atoms, halogen atom, hydroxy group, nitro group, and alkoxy group having 1 to 4 carbon atoms. The substituted phenyl group may have 1 to 5 substituents on its ring, and the substituent may be present on any position.

The substituted phenyl group includes a 2-methylphenyl group, 3-methylphenyl group, 4-methylphenyl group, 2,3-dimethylphenyl group, 2,4-dimethylphenyl group, 2,5-dimethylphenyl group, 2,6-dimethylphenyl group, 2-chlorophenyl group, 3-chlorophenyl group, 4-chlorophenyl group, 2-hydroxyphenyl group, 3-hydroxyphenyl group, 4-hydroxyphenyl group, 2-nitrophenyl group, 3-nitrophenyl group, 4-nitrophenyl group, 2-methoxyphenyl group, 3-methoxyphenyl group, and 4-methoxyphenyl group.

The optionally substituted alkenyl group represented by X in the benzaldehyde compound (1) may be an unsubstituted alkenyl group, or an alkenyl group substituted with a halogen atom, hydroxy group, nitro group, amino group, alkoxy group or the like. The unsubstituted alkenyl group usually has about 2 to 12 carbon atoms. The substituted alkenyl group has a substituent carried on an alkenyl group usually having about 2 to 12 carbon atoms.

Examples of the optionally substituted alkenyl group include unsubstituted alkenyl groups such as a vinyl group, allyl group, 1-butenyl group, 1-pentenyl group, 1-hexenyl group and 1-octenyl group, and 3-hydroxy-1-propenyl group, 3-nitro-1-propenyl group, 3-amino-1-propenyl group and 3-methoxy-1-propenyl group.

The optionally substituted alkynyl group represented by X in the benzaldehyde compound (1) may be an unsubstituted alkynyl group, or an alkynyl group substituted with a halogen atom, hydroxy group, nitro group, amino group, alkoxy group or the like. The unsubstituted alkynyl group usually has about 2 to 12 carbon atoms. The substituted alkynyl group has a substituent carried on an alkynyl group usually having about 2 to 12 carbon atoms.

Examples of the optionally substituted alkynyl group include unsubstituted alkynyl groups such as 1-ethynyl group, propargyl group, 1-butynyl group, 1-pentynyl group, 1-hexynyl group and 1-octynyl group, and 3-hydroxy-1-propynyl group, 3-nitro-1-propynyl group, 3-amino-1-propynyl group and 3-methoxy-1-propynyl group.

Examples of the optionally substituted phenyl group represented by X in the benzaldehyde compound (1) include the same phenyl groups as mentioned for $R^2$.

The optionally substituted phenoxy group represented by X in the benzaldehyde compound (1) may be unsubstituted phenoxy group, or a phenoxy group substituted with an alkyl group, halogen atom, hydroxy group, nitro group, amino group or the like. The substituted phenoxy group may have 1 to 5 substituents on its ring, and the substituent may be present on any position.

The optionally substituted phenoxy group includes a phenoxy group, 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 2-chlorophenoxy group, 3-chlorophenoxy group, 4-chlorophenoxy group, 2-hydroxyphenoxy group, 3-hydroxyphenoxy group, 4-hydroxyphenoxy group, 2-nitrophenoxy group, 3-nitrophenoxy group, 4-nitrophenoxy group, 2-methoxyphenoxy group, 3-methoxyphenoxy group and 4-methoxyphenoxy group.

The optionally substituted amino group represented by X in the benzaldehyde compound (1) may be an unsubstituted amino group, or an amino group substituted with an alkyl group or the like. The substituted amino group includes a methylamino group and dimethylamino group.

The above-described X represents preferably an optionally substituted alkyl group or an optionally substituted phenyl group, more preferably a group represented by the formula (3) or an unsubstituted phenyl group, further preferably a group represented by the formula (3).

The above-described group represented by the formula (3) is preferably an (alkyl substituted phenoxy)methyl group, more preferably a 2,5-dimethylphenoxymethyl group.

As $R^1$ in the benzaldehyde compound (1), the optionally substituted alkyl group, optionally substituted alkenyl group, optionally substituted alkynyl group, optionally substituted phenyl group, optionally substituted phenoxy group and optionally substituted amino group may respectively be the same substituents as mentioned for X, and the same substituents as described above can be mentioned.

The optionally substituted alkoxy group represented by $R^1$ in the benzaldehyde compound (1) may be an unsubstituted alkoxy group, or an alkoxy group substituted with a halogen atom, hydroxy group, nitro group, amino group, alkoxy group or the like. The unsubstituted alkoxy group usually has about 1 to 12 carbon atoms. The substituted alkoxy group has a substituent carried on an alkoxy group usually having about 1 to 12 carbon atoms.

Examples of the optionally substituted alkoxy group include unsubstituted alkoxy groups such as methoxy group, ethoxy group, n-propoxy group, isopropoxy group, n-butoxy group, isobutoxy group, s-butoxy group, t-butoxy group, 1-hexyloxy group, 1-octyloxy group, and a trifluoromethyloxy group, hydroxymethyloxy group, nitromethyloxy group, aminomethyloxy group and methoxymethyloxy group.

In the formula (1), m represents preferably an integer of 0 to 2, more preferably 0.

In the present invention, the benzaldehyde compound (1) is preferably a compound represented by the formula (1) in which m=0 and X represents an optionally substituted alkyl group or an optionally substituted phenyl group, more preferably a compound represented by the formula (1) in which m=0 and X represents a group represented by the formula (3), further preferably a compound represented by the formula (1) in which m=0 and X represents an (alkyl substituted phenoxy)methyl group, in particular preferably 2-(2,5-dimethylphenoxymethyl)benzaldehyde.

Hydrogen cyanide to be used in the present invention may be gaseous or liquid. In the present invention, an aqueous hydrogen cyanide solution may be used as the hydrogen cyanide, alternatively, a solution prepared by dissolving hydrogen cyanide in an organic solvent may be used. Examples of the organic solvent include aromatic hydrocarbons such as benzene, toluene, xylene and chlorobenzene; aliphatic hydrocarbons such as n-hexane and n-heptane; alicyclic hydrocarbons such as cyclopentane and cyclohexane; ethers such as diethyl ether, dibutyl ether, tetrahydrofuran and tetrahydropyran; alcohols such as methanol and ethanol; and nitrile solvents such as acetonitrile.

The use amount of hydrogen cyanide is 1.2 to 5 mol, preferably 1.2 to 3 mol, more preferably 1.2 to 2.5 mol, further preferably 1.2 to 1.9 mol with respect to 1 mol of benzaldehyde compound (1). When the use amount of hydrogen cyanide is less than 1.2 mol with respect to 1 mol of benzaldehyde compound (1), the conversion of benzaldehyde compound (1) tends to be lower. The reaction of benzaldehyde compound (1) and hydrogen cyanide occurs theoretically at a molar ratio of 1:1, however, benzaldehyde compound (1) having a prescribed substituent at an ortho position is so low in reactivity that it is difficult for the compound to show sufficient conversion even if the reaction time is elongated or the reaction temperature is raised. Too large use amount of hydrogen cyanide is undesirable because of unreacted hydrogen cyanide remains in a larger amount and its production cost increases.

In the present invention, benzaldehyde compound (1) and hydrogen cyanide are reacted in the presence of an organic base. In the present invention, the organic base is supposed to promote the conversion of benzaldehyde compound (1).

Examples of the above-described organic base include amine compounds such as cyclic amines and aliphatic amines. Specific examples of the above-described organic base include diethylamine, triethylamine, tripropylamine, pyridine, 1-methylimidazole, 1,2-dimethylimidazol. Of them, aliphatic amines are preferable and triethylamine is more preferable since the reactivity of hydrogen cyanide can be enhanced.

In the present invention, if necessary two or more of the above-described organic bases may be used.

The use amount of the organic base is usually 0.001 mol or more to 1 mol or less with respect to 1 mol of benzaldehyde compound (1). The preferable lower limit of the use amount is 0.005 mol and the preferable upper limit of the use amount is 0.1 mol with respect to 1 mol of benzaldehyde compound (1).

The reaction of benzaldehyde compound (1) and hydrogen cyanide is carried out in an organic solvent. As the organic solvent, those in-soluble in water are preferable, and examples thereof include aromatic hydrocarbons such as benzene, toluene, xylene and chlorobenzene; aliphatic hydrocarbons such as n-hexane and n-heptane; alicyclic hydrocarbons such as cyclopentane and cyclohexane; ethers such as diethyl ether, dibutyl ether, tetrahydrofuran and tetrahydropyran. Of them, aromatic hydrocarbons are preferable and xylene is more preferable in view of easy handling and cost. In the present invention, if necessary, two or more organic solvents can be used. The use amount of the organic solvent is usually 0.5 to 10 parts by weight, preferably 1 to 5 parts by weight with respect to 1 part by weight of benzaldehyde compound (1).

In this reaction, lower water concentration in the reaction system is more preferable since water lowers the reactivity of hydrogen cyanide.

In the present invention, the reaction of benzaldehyde compound (1) and hydrogen cyanide is carried out in general by mixing an organic solvent, organic base, benzaldehyde compound (1) and hydrogen cyanide. The method of mixing an organic solvent, organic base, benzaldehyde compound (1) and hydrogen cyanide includes, for example, methods in which hydrogen cyanide is added at one time or added dropwise to a mixture of an organic solvent, organic base and benzaldehyde compound (1). Of them, a method which comprises dropping hydrogen cyanide is preferable. In the case of dropping of hydrogen cyanide, the dropping time is usually 0.5 to 20 hours, preferably 1 to 10 hours.

The reaction temperature is usually −20 to 50° C., preferably 0 to 30° C. After mixing of the whole amount of hydrogen cyanide, benzaldehyde compound (1) is usually stirred while insulating heat, thereby progressing the reaction. Also when dropping hydrogen cyanide, the reaction can be progressed by maintaining the temperature during dropping at the above-described reaction temperature.

Mandelonitrile compound (2) obtained by the above-described reaction can be purified, if necessary, according to conventionally known means. The mandelonitrile compound (2) can be purified, for example, by adding an acidic water such as hydrochloric acid (aqueous solution of hydrogen chloride) and aqueous sulfuric acid solution to a reaction mixture obtained by the reaction, then, separating oil and water, and removing a solvent and the like from the resultant oil layer.

EXAMPLES

Examples of the present invention will be shown below, but the present invention is not limited to them. The amounts of benzaldehyde compound (1) and mandelonitrile compound (2) in the reaction mixture were analyzed by liquid chromatography (measuring device: LC-10A, SHIMADZU), and the conversion and residual ratio of benzaldehyde compound (1) and the yield of mandelonitrile compound (2) were calculated.

Example 1

Into a 300 ml flask was charged 30.0 g (0.12 mol) of 2-(2,5-dimethylphenoxymethyl)benzaldehyde [compound represented by the formula (1) in which X represents a 2,5-dimethylphenoxymethyl group and m=0], 75.00 g of xylene and 0.13 g (0.0012 mol) of triethylamine and they were mixed, then, cooled down to 15° C. while stirring. Then, into the mixture, 4.05 g (0.15 mol) of hydrogen cyanide was dropped over a period of 2 hours, thereby adding hydrogen cyanide in an amount of 1.2 mol with respect to 1 mol of 2-(2,5-dimethylphenoxymethyl)benzaldehyde. After completion of dropping, the reaction mixture was stirred at 15° C. for 4 hours. This reaction mixture was analyzed to find that the conversion of 2-(2,5-dimethylphenoxymethyl)benzaldehyde was 96.6%, the residual ratio thereof was 3.4%, and the yield of 2-(2,5-dimethylphenoxymethyl)mandelonitrile [compound represented by the formula (2) in which X represents a 2,5-dimethylphenoxymethyl group and m=0] was 96.6%.

Example 2

Into a 300 ml flask was charged 30.00 g (0.12 mol) of 2-(2,5-dimethylphenoxymethyl)benzaldehyde, 75.00 g of xylene and 0.13 g (0.0012 mol) of triethylamine and they were mixed, then, cooled down to 15° C. while stirring. Then, into the mixture, 5.06 g (0.19 mol) of hydrogen cyanide was dropped over a period of 2 hours, thereby adding hydrogen cyanide in an amount of 1.5 mol with respect to 1 mol of 2-(2,5-dimethylphenoxymethyl)benzaldehyde. After completion of dropping, the reaction mixture was stirred at 15° C. for 4 hours. This reaction mixture was analyzed to find that the conversion of 2-(2,5-dimethylphenoxymethyl)benzaldehyde was 98.8%, the residual ratio thereof was 1.2% and the yield of 2-(2,5-dimethylphenoxymethyl)mandelonitrile was 98.8%.

Example 3

Into a 300 ml flask was charged 50.00 g (0.21 mol) of 2-(2,5-dimethylphenoxymethyl)benzaldehyde, 125.00 g of xylene and 0.21 g (0.0021 mol) of triethylamine and they were mixed, then, cooled down to 15° C. while stirring. Then, into the mixture, 11.25 g (0.42 mol) of hydrogen cyanide was dropped over a period of 2 hours, thereby adding hydrogen cyanide in an amount of 2.0 mol with respect to 1 mol of 2-(2,5-dimethylphenoxymethyl)benzaldehyde. After completion of dropping, the reaction mixture was stirred at 15° C. for 4 hours. This reaction mixture was analyzed to find that the conversion of 2-(2,5-dimethylphenoxymethyl)benzaldehyde was 99.0%, the residual ratio thereof was 1.0% and the yield of 2-(2,5-dimethylphenoxymethyl)mandelonitrile was 99.0%.

Example 4

Into a 300 ml flask was charged 3.00 g (0.016 mol) of 2-biphenylaldehyde [compound represented by the formula (1) in which X represents a phenyl group and m=0], 7.50 g of xylene and 0.017 g (0.00016 mol) of triethylamine and they were mixed, then, cooled down to 15° C. while stirring. Then, into the mixture, 0.89 g (0.033 mol) of hydrogen cyanide was dropped over a period of 2 hours, thereby adding hydrogen cyanide in an amount of 2.0 mol with respect to 1 mol of 2-biphenylaldehyde. After completion of dropping, the reaction mixture was stirred at 15° C. for 1 hour. This reaction mixture was analyzed to find that the conversion of 2-biphenylaldehyde was 95.6%, the residual ratio thereof was 4.4% and the yield of 2-phenylmandelonitrile [compound represented by the formula (2) in which X represents a phenyl group and m=0] was 95.6%.

Reference Example 1

Into a 300 ml flask was charged 10.00 g (0.066 mol) of 2-ethoxybenzaldehyde [compound represented by the formula (1) in which X represents an ethoxy group and m=0], 25.00 g of xylene and 0.07 g (0.00066 mol) of triethylamine and they were mixed, then, cooled down to 15° C. while stirring. Then, into the mixture, 3.60 g (0.13 mol) of hydrogen cyanide was dropped over a period of 2 hours, thereby adding hydrogen cyanide in an amount of 2.0 mol with respect to 1 mol of 2-ethoxybenzaldehyde. After completion of dropping, the reaction mixture was stirred at 15° C. for 1 hour. This reaction mixture was analyzed to find that the conversion of 2-ethoxybenzaldehyde was 90.1%, the residual ratio thereof was 9.9% and the yield of 2-ethoxymandelonitrile [compound represented by the formula (2) in which X represents an ethoxy group and m=0] was 90.1%.

Comparative Example 1

Into a 300 ml flask was charged 30.00 g (0.12 mol) of 2-(2,5-dimethylphenoxymethyl)benzaldehyde, 75.00 g of xylene, 0.30 g of sodium acetate and 12.60 g of water and they were mixed. In this time point, pH of the aqueous phase was 6.4. The mixture was cooled down to 15° C. while stirring. Then, into the mixture, hydrogen cyanide (3.37 g, 0.12 mol) was dropped over a period of 2 hours, thereby adding hydrogen cyanide in an amount of 1.0 mol with respect to 1 mol of 2-(2,5-dimethylphenoxymethyl)benzaldehyde. After completion of dropping, the reaction mixture was stirred at 15° C. for 4 hours. This reaction mixture was analyzed to find that 2-(2,5-dimethylphenoxymethyl)benzaldehyde did not reacted completely [the conversion of 2-(2,5-dimethylphenoxymethyl)benzaldehyde was 0%, the residual ratio thereof was 100%].

Comparative Example 2

Into a 300 ml flask was charged 44.00 g (0.16 mol) of 2-(2,5-dimethylphenoxymethyl)benzaldehyde, 125.00 g of xylene and 0.21 g (0.0021 mol) of triethylamine and they were mixed, then, cooled down to 15° C. while stirring. Then, into the mixture, hydrogen cyanide (4.36 g, 0.16 mol) was dropped over a period of 2 hours, thereby adding hydrogen cyanide in an amount of 1.0 mol with respect to 1 mol of 2-(2,5-dimethylphenoxymethyl)benzaldehyde. After completion of dropping, the reaction mixture was stirred at 15° C. for 4 hours. This reaction mixture was analyzed to find that the conversion of 2-(2,5-dimethylphenoxymethyl)benzaldehyde was 65.8%, the residual ratio thereof was 34.2% and the yield of 2-(2,5-dimethylphenoxymethyl)mandelonitrile was 65.8%.

Comparative Example 3

Into a 300 ml flask was charged 30.00 g (0.12 mol) of 2-(2,5-dimethylphenoxymethyl)benzaldehyde, 75.00 g of xylene and 0.13 g (0.0012 mol) of triethylamine and they were mixed, then, cooled down to 20° C. while stirring. Then, into the mixture, hydrogen cyanide (3.37 g, 0.12 mol) was dropped over a period of 2 hours, thereby adding hydrogen cyanide in an amount of 1.0 mol with respect to 1 mol of 2-(2,5-dimethylphenoxymethyl)benzaldehyde. After completion of dropping, the reaction mixture was stirred at 20° C. for 4 hours. This reaction mixture was analyzed to find that the conversion of 2-(2,5-dimethylphenoxymethyl)benzaldehyde was 71.9%, the residual ratio thereof was 28.1% and the yield of 2-(2,5-dimethylphenoxymethyl)mandelonitrile was 71.9%.

INDUSTRIAL APPLICABILITY

According to the present invention, benzaldehyde compound (1) can be reacted with good conversion to produce mandelonitrile compound (2) in good yield. The mandelonitrile compound is useful, for example, as a raw material for medicines and agricultural chemicals.

The invention claimed is:

1. A method for producing a compound represented by the following formula (2)

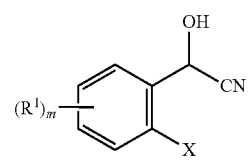

(wherein, X, $R^1$ and m represent respectively the same meaning as described below) which comprises reacting a compound represented by the following formula (1)

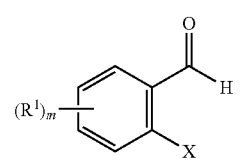

(wherein, X represents the following formula (3)

(wherein $R^2$ represents an optionally substituted phenyl group); $R^1$ represents an optionally substituted alkyl group, optionally substituted alkenyl group, optionally substituted alkynyl group, optionally substituted alkoxy group, optionally substituted phenyl group, optionally substituted phenoxy group, optionally substituted amino group, hydroxy group, nitro group or halogen atom; m represents an integer of 0 to 4, and when m represents an integer of 2 to 4, $R^1$ s may be the same or different from each other)

with hydrogen cyanide in an amount of 1.2 to 5 mol with respect to 1 mol of the compound, in the presence of an organic base, in an organic solvent.

2. The production method according to claim 1, wherein m represents 0 in the formula (1).

3. The production method according to claim 1, wherein the compound represented by the formula (1) is 2-(2,5-dimethylphenoxymethyl)benzaldehyde.

4. The production method according claim 1, wherein the organic base is an amine compound.

5. The production method according claim 1, wherein the organic solvent is an aromatic hydrocarbon.

* * * * *